(12) United States Patent
Zerban et al.

(10) Patent No.: US 8,354,543 B2
(45) Date of Patent: *Jan. 15, 2013

(54) PROCESS FOR THE PREPARATION OF 4-(BENZIMIDAZOLYLMETHYLAMINO)-BENZAMIDES AND THE SALTS THEREOF

(75) Inventors: Georg Zerban, Ingelheim am Rhein (DE); Arndt Hausherr, Mainz (DE); Kerstin Schlarb, Appenheim (DE); Rainer Hamm, Ingelheim am Rhein (DE); Gunter Koch, Schwabenheim (DE); Bjoem Weyell, Aspisheim (DE); Heinz-Peter Schmitt, Ingelheim and Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 320 days.

This patent is subject to a terminal disclaimer.

(21) Appl. No.: 12/769,718

(22) Filed: Apr. 29, 2010

(65) Prior Publication Data
US 2010/0210845 A1 Aug. 19, 2010

Related U.S. Application Data

(63) Continuation of application No. 11/614,304, filed on Dec. 21, 2006, now abandoned.

(30) Foreign Application Priority Data

Dec. 21, 2005 (DE) .......................... 10 2005 061 623

(51) Int. Cl.
C07D 235/16 (2006.01)
(52) U.S. Cl. ................................. 548/309.7; 546/273.4
(58) Field of Classification Search ............... 548/309.7; 546/273.4
See application file for complete search history.

(56) References Cited

U.S. PATENT DOCUMENTS

| | | | |
|---|---|---|---|
| 6,087,380 A | 7/2000 | Hauel et al. | |
| 6,248,770 B1 | 6/2001 | Ries et al. | |
| 6,451,832 B2 | 9/2002 | Ries et al. | |
| 7,202,368 B2 | 4/2007 | Zerban et al. | |
| 7,459,566 B2 | 12/2008 | Zerban et al. | |
| 7,880,016 B2 * | 2/2011 | Zerban et al. | 548/309.7 |
| 2007/0149589 A1 | 6/2007 | Zerban et al. | |
| 2007/0185173 A1 | 8/2007 | Zerban et al. | |
| 2010/0099882 A1 | 4/2010 | Broeder et al. | |

FOREIGN PATENT DOCUMENTS

| | | |
|---|---|---|
| CA | 2 277 949 A1 | 8/1998 |
| CA | 2 337 804 A1 | 1/2000 |
| CA | 2 393 916 A1 | 7/2001 |
| DE | 199 62 329 A1 | 6/2001 |
| EP | 1 609 784 A1 | 12/2005 |
| WO | 98/37075 A1 | 8/1998 |
| WO | 00/01704 A2 | 1/2000 |
| WO | 2006/000353 A1 | 1/2006 |
| WO | 2009/118321 A1 | 10/2009 |
| WO | 2009/118322 A1 | 10/2009 |
| WO | 2009/153214 A1 | 12/2009 |
| WO | 2009/153215 A1 | 12/2009 |
| WO | 2010/007016 A1 | 1/2010 |

OTHER PUBLICATIONS

Anbazhagan, et al: "Direct conversion of amidoximes to amidines via transfer hydogenation" 2003, p. 2467-2469, No. 16, Synthesis, department of Chemistry, Georgia State University, Atlanta, USA.

Bolton, et al: "3-Substituted-1,2,4-oxadiazolin-5-one; A useful amidine precursor and protecting group" 1995, p. 4471-4474, vol. 36, No. 25, Tetrahedron Letters, Elsevier, Amsterdam NL, Glaxo Research and Development Ltd, Glaxo Medicines Research Centre, Stevenage, UK.

Liao, et al: "New selective and potent 5-HtT 1B/1D antagonist: chemistry and pharmacological evaluation of N-piperazinylphenyl biphenylcarboxamides and biphenylsufonamides" 2000, p. 517-525, vol. 43,Journal of Medicinal Chemistry, American Chemical Society, Department of Medicinal Chemistry, Center for Pharmacy, University of Groningen, Groningen, The Netherlands, Preclinical Pharmaceutical Research, Merck KGaA, Dartstadt, Germany and Department of Medical Biochemistry, University of Goteborg, Goteborg, Sweden.

Peterlin-Masic, et al: "Arginine mimetics" 2001, p. 7073-7105, vol. 57, No. 33, Tetrahedron, Elsevier Science Publishers, Amsterdam, NL, Department of Pharmacy, University of Ljubljana, Ljubjana, Slovenia.

* cited by examiner

*Primary Examiner* — Laura L. Stockton
(74) *Attorney, Agent, or Firm* — Michael P. Morris; Wendy A. Petka

(57) ABSTRACT

The invention relates to a process for preparing an optionally substituted 4-benzimidazol-2-ylmethylamino)-benzamidine, characterized in that
(a) an optionally correspondingly substituted diaminobenzene is condensed with 2-[4-(1,2,4-oxadiazol-5-on-3-yl)-phenylamino]-acetic acid,
(b) i) the product thus obtained is hydrogenated and
ii) optionally the amidino group is carbonylated, without isolating the intermediate product of the hydrogenation beforehand;
as well as a process for preparing a salt of an optionally substituted 4-(benzimidazol-2-ylmethylamino)-benzamidine, wherein
(a) an optionally correspondingly substituted diaminobenzene is condensed with 2-[4-(1,2,4-oxadiazol-5-on-3-yl)-phenylamino]-acetic acid,
(b) the product thus obtained is hydrogenated, and
(c) i) optionally the amidino group is carbonylated and
ii) without prior isolation of the intermediate product of the carbonylation the desired salt is isolated.

3 Claims, No Drawings

PROCESS FOR THE PREPARATION OF 4-(BENZIMIDAZOLYLMETHYLAMINO)-BENZAMIDES AND THE SALTS THEREOF

RELATED APPLICATIONS

This application is a continuation application of U.S. application Ser. No. 11/614,304, filed Dec. 21, 2006, which claims priority to German Application DE 10 2005 061 623.2 filed Dec. 21, 2005, the contents of which are hereby incorporated by reference.

BACKGROUND TO THE INVENTION

1. Technical Field

The invention relates to a process for preparing an optionally substituted 4-(benzimidazol-2-ylmethylamino)-benzamidine, wherein
(a) an optionally correspondingly substituted diaminobenzene is condensed with 2-[4-(1,2,4-oxadiazol-5-on-3-yl)-phenylamino]-acetic acid and
(b) i) the product thus obtained is hydrogenated and
  ii) optionally the amidino group is carbonylated without isolating the intermediate product of the hydrogenation beforehand.
The 4-(benzimidazol-2-ylmethylamino)-benzamidine thus obtained may subsequently be converted into a salt.

Moreover, the invention relates to a process for preparing a salt of an optionally substituted 4-(benzimidazol-2-ylmethylamino)-benzamidine, wherein
(a) an optionally correspondingly substituted diaminobenzene is condensed with 2-[4-(1,2,4-oxadiazol-5-on-3-yl)-phenylamino]-acetic acid,
(b) the product thus obtained is hydrogenated, and
(c) i) optionally the amidino group is carbonylated and
  ii) without prior isolation of the intermediate product of the carbonylation the desired salt is isolated.

2. Prior Art

Substituted (4-benzimidazol-2-ylmethylamino)-benzamidines, particularly 1-methyl-2-[N-[4-(N-n-hexyloxycarbonylamidino)phenyl]-amino-methyl]-benzimidazol-5-yl-carboxylic acid-N-(2-pyridyl)-N-(2-ethoxycarbonylethyl)-amide are already known from International Patent Application WO 98/37075 as active substances with a thrombin-inhibiting and thrombin time prolonging activity.

The main types of indication for the compound of chemical formula I are the postoperative prevention of deep vein thrombosis and the prevention of stroke (prevention of stroke due to atrial fibrillation, SPAF for short).

In WO 98/37075 it is proposed that the substituted (4-benzimidazol-2-ylmethylamino)-benzamidines be prepared by reacting the corresponding substituted (4-benzimidazol-2-ylmethylamino)-benzonitriles with ammonia. This process is highly complex from the point of view of production technology and results in a high loading of acids that have to be disposed of.

The aim of the present invention was to indicate an alternative method of preparing the substituted (4-benzimidazol-2-ylmethylamino)-benzamidines, by which this technologically complex step could be avoided.

BRIEF SUMMARY OF THE INVENTION

Surprisingly it has now been found that the substituted 4-(benzimidazol-2-ylmethylamino)-benzamidines can be produced in high yields and using inexpensive adjuvants if
(a) an optionally correspondingly substituted diaminobenzene is condensed with 2-[4-(1,2,4-oxadiazol-5-on-3-yl)-phenylamino]-acetic acid and
(b) i) the product thus obtained is hydrogenated, and
  ii) optionally the amidino group is carbonylated, preferably with an alkyl halogen formate in the presence of a base, particularly with n-hexylchloroformate, without isolating the intermediate product of the hydrogenation beforehand.
The 4-(benzimidazol-2-ylmethylamino)-benzamidine thus obtained may subsequently be converted into a salt.

It has also surprisingly been found that the salts of optionally substituted 4-(benzimidazol-2-ylmethylamino)-benzamidines can be prepared in high yields and using inexpensive adjuvants if
(a) an optionally correspondingly substituted diaminobenzene is condensed with 2-[4-(1,2,4-oxadiazol-5-on-3-yl)-phenylamino]-acetic acid,
(b) the product thus obtained is hydrogenated, and
(c) i) optionally the amidino group is carbonylated and
  ii) without prior isolation of the intermediate product of the carbonylation the desired salt is isolated.

DETAILED DESCRIPTION OF THE INVENTION

A process for preparing an optionally substituted 4-(benzimidazol-2-ylmethylamino)-benzamidine of formula (I) is preferred

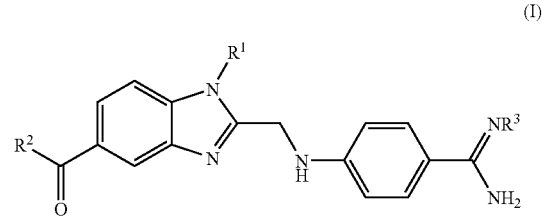

(I)

wherein
$R^1$ denotes a $C_{1-6}$-alkyl or $C_{3-7}$-cycloalkyl group,
$R^2$
(i) denotes a $C_{1-6}$-alkyl group, a $C_{3-7}$-cycloalkyl group optionally substituted by a $C_{1-3}$-alkyl group, while the $C_{1-3}$-alkyl group may additionally be substituted by a carboxyl group or by a group which may be converted in vivo into a carboxy group, or
(ii) denotes an $R^{21}NR^{22}$ group, wherein
  $R^{21}$ denotes a $C_{1-6}$ alkyl group which may be substituted by a carboxy, $C_{1-6}$ alkoxycarbonyl, benzyloxycarbonyl, $C_{1-3}$-alkylsulphonylaminocarbonyl, phenylsulphonylaminocarbonyl, trifluorosulphonylamino, trifluorosulphonylaminocarbonyl or 1H-tetrazolyl group, a $C_{2-4}$-alkyl group substituted by a hydroxy, phenyl-$C_{1-3}$-alkoxy, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkylamino or N—($C_{1-3}$-alkyl)-$C_{1-3}$-alkoxycarbonyl-$C_{1-3}$-alkylamino group, while in the above-mentioned groups the carbon atom in the α-position to the adjacent nitrogen atom cannot be substituted, or
  a piperidinyl group optionally substituted by a $C_{1-3}$-alkyl group, and
  $R^{22}$ denotes a hydrogen atom, a $C_{1-6}$-alkyl group, a $C_{3-7}$-cycloalkyl group optionally substituted by a $C_{1-3}$-alkyl group, or a $C_{3-6}$-alkenyl or $C_{3-6}$-alkynyl group, while the unsaturated moiety may not be linked directly to the nitrogen atom of the $R^{21}NR^{22}$ group, a phenyl group optionally substituted by a fluorine, chlorine or bromine atom, by a $C_{1-3}$-alkyl or $C_{1-3}$-alkoxy group, or a benzyl, oxazolyl, isoxazolyl, thiazolyl, isothiazolyl, pyrazolyl, pyridinyl, pyrimidinyl, pyrazinyl, pyridazinyl, pyrrolyl, thienyl or imidazolyl group optionally substituted by a $C_{1-3}$-alkyl group, or $R^{21}$ and $R^{22}$ together with the nitrogen atom between them denote a 5- to 7-membered cycloalkyleneimino group optionally substituted by a carboxy or $C_{1-4}$-alkoxycarbonyl group, to which additionally a phenyl ring may be fused, and $R^3$ denotes a hydrogen atom, a $C_{1-6}$-alkoxycarbonyl, cyclohexyloxycarbonyl, phenyl-$C_{1-3}$-alkoxycarbonyl, benzoyl, p-$C_{1-3}$-alkyl-benzoyl or pyridinoyl group, wherein the ethoxy moiety in the 2 position of the above-mentioned $C_{1-9}$-alkoxycarbonyl group may additionally be substituted by a $C_{1-3}$-alkylsulphonyl or 2-($C_{1-3}$-alkoxy)-ethyl group, while in step (a) a phenyldiamine of formula (II)

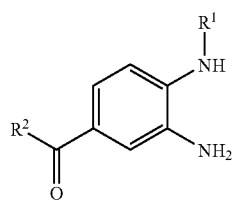

(II)

wherein $R^1$ and $R^2$ have the meanings given for formula (I), is reacted with 2-[4-(1,2,4-oxadiazol-5-on-3-yl)-phenylamino]-acetic acid, the resulting product of formula (III)

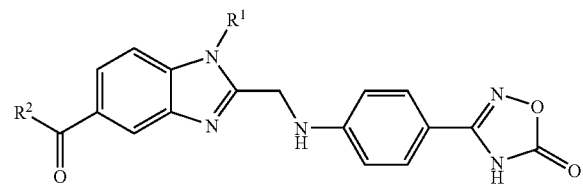

(III)

wherein $R^1$ and $R^2$ have the meanings given for formula (I), is hydrogenated in step (b)i), and subsequently, without any prior isolation of the hydrogenation product, the compound of formula (I) thus obtained wherein $R^3$ denotes hydrogen is optionally reacted in step (b)ii) with a compound of formula (IV)

$R^3$—X (IV)

wherein $R^3$ has the meaning given for formula (I), and X denotes a suitable leaving group.

The 4-(benzimidazol-2-ylmethylamino)-benzamidine thus obtained may if desired subsequently be converted into a salt, particularly into a pharmaceutically acceptable salt, in another step (c).

Another preferred process for preparing a salt of an optionally substituted 4-(benzimidazol-2-ylmethylamino)-benzamidine of formula (I)

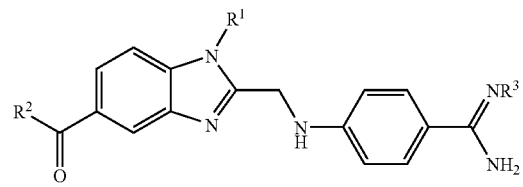

(I)

wherein $R^1$ to $R^3$ are as hereinbefore defined, comprises the following steps:
(a) reacting a phenyldiamine of formula (II)

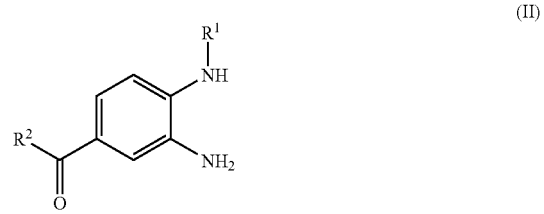

(II)

wherein $R^1$ and $R^2$ have the meanings given for formula (I), with 2-[4-(1,2,4-oxadiazol-5-on-3-yl)-phenylamino]-acetic acid,
(b) hydrogenating the product of formula (III) thus obtained

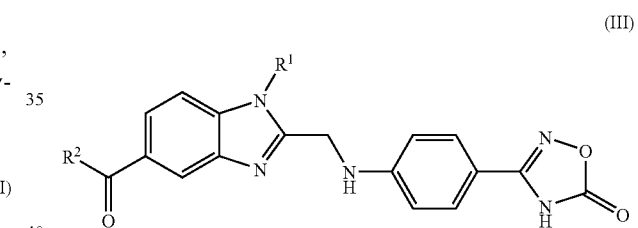

(III)

wherein $R^1$ and $R^2$ have the meanings given for formula (I), and
(c) i) reacting the compound of formula (I) thus obtained wherein $R^3$ denotes hydrogen with a compound of formula (IV)

$R^3$—X (IV)

wherein $R^3$ has the meaning given for formula (I) and X denotes a suitable leaving group, and
ii) precipitating the desired salt of the compound of formula (I) thus obtained, without previously isolating the carbonylation product.

Particularly preferred are the processes according to the invention for preparing the compounds of formula (I) or the salts thereof, wherein
$R^1$ denotes a $C_{1-3}$-alkyl group,
$R^2$ denotes an $R^{21}NR^{22}$ group, wherein
  $R^{21}$ denotes a $C_{1-3}$ alkyl group which may be substituted by a carboxy, $C_{1-3}$ alkoxycarbonyl, and
  $R^{22}$ denotes a hydrogen atom, a $C_{1-3}$-alkyl group, a pyridinyl group optionally substituted by a $C_{1-3}$-alkyl group, and
$R^3$ denotes a hydrogen atom, a $C_{1-8}$-alkoxycarbonyl group.

Most preferred are the processes according to the invention for preparing the compound of formula (I) or the salts thereof, wherein $R^1$ denotes a methyl group, $R^2$ denotes an $R^{21}NR^{22}$ group, wherein $R^{21}$ denotes an ethyl group which is substituted by an ethoxycarbonyl group, and $R^{22}$ denotes a pyridin-2-yl group, and $R^3$ denotes an n-hexyloxycarbonyl group.

Preferred salts are the methanesulphonate, chloride, maleate, tartrate, salicylate, citrate and malonate of the compound of formula (I). A particularly preferred salt is the methanesulphonate.

The following embodiments (A) to (F) of the process according to the invention are preferred:

(A) The condensation of step (a) is carried out in the presence of an inert diluent and a water-binding agent.

The correspondingly substituted diaminobenzenes of formula (II) are known e.g. from International Patent Application WO 98/37075, e.g. from Example 25 (Steps a and b), or may be prepared analogously to those described therein. For the hydrogenation of the nitro precursor compound for preparing the diaminobenzene of formula (II) the solvent used may be, for example, toluene, isopropanol, triethylamine, ethanol, butyl acetate, ethyl acetate, methanol or mixtures of these solvents. Preferably, the hydrogenation is carried out under a hydrogen pressure of 1 to 20 bar, but higher pressures are also possible. The concentration of the aromatic nitrogen compound (educt) is conveniently 10 to 40 wt. %; it is more preferably present in a concentration of 20 to 30 wt. %. The catalyst used may be for example 5-10% palladium on charcoal, while preferably 2-20 wt. % of wet charcoal-palladium catalyst is used, based on the aromatic nitrogen compound, which corresponds to about 0.05-1 wt. % palladium based on the aromatic nitrogen compound. Particularly preferably, 3-amino-4-methylaminobenzoic acid amides are used, particularly 3-amino-4-methylaminobenzoic acid-N-(2-pyridyl)-N-(2-ethoxycarbonylethyl)-amide.

The inert diluents used may be both aprotic apolar solvents—such as e.g. aliphatic or aromatic, optionally halogenated hydrocarbons—or aprotic polar solvents such as e.g. ethers and/or amides or lactams and/or mixtures thereof. The aprotic apolar solvents used are preferably branched or unbranched $C_5$-$C_8$ aliphatic alkanes, $C_4$-$C_{10}$ cycloalkanes, $C_1$-$C_6$ aliphatic haloalkanes, $C_6$-$C_{10}$ aromatic alkanes or mixtures thereof. It is particularly preferable to use alkanes such as pentane, hexane or heptane, cycloalkanes such as cyclohexane or methylcyclohexane, haloalkanes such as dichloromethane, aromatic alkanes such as benzene, toluene or xylene or mixtures thereof. Suitable aprotic solvents are polar ethers such as, for example, tetrahydrofuran (THF), methyltetrahydrofuran, dioxane, tert-butyl-methylether or dimethoxyethylether or amides such as, for example, dimethylformamide, or lactams such as N-methylpyrrolidone, for example.

Water-binding agents which may be used are hygroscopic salts, inorganic or organic acids or the acid chlorides thereof, anhydrides of inorganic or organic acids, anhydrides of alkanephosphonic acids, molecular sieves or urea derivatives. 1,1'-carbonyldiimidazoles and alkanephosphonic anhydrides are preferred, while alkanephosphonic anhydrides are particularly preferred.

In a preferred embodiment 1,1'-carbonyldiimidazole is suspended in THF and heated. 2-[4-(1,2,4-Oxadiazol-5-on-3-yl)-phenylamino]-acetic acid is added. The correspondingly substituted diaminobenzene is added to THF. The reaction mixture is stirred at about 50° C. and subsequently, after the addition of acetic acid, evaporated down and mixed with water and the solid substance is filtered off, washed and dried.

In a second particularly preferred embodiment, alkanephosphonic anhydrides are added, in the presence of an organic base, preferably a tert. amine such as e.g. DIPEA, to a solution of 2-[4-(1,2,4-oxadiazol-5-on-3-yl)-phenylamino]-acetic acid and correspondingly substituted diaminobenzene in THF. The reaction mixture is stirred, preferably at temperatures between −10 and 50° C., and subsequently, after the addition of acetic acid, evaporated down. It is combined with ethanol/water and optionally a filter aid, for example kieselguhr (e.g. Clarcel®), and filtered hot. Then the substance precipitated from the cooled solution is filtered off, washed and dried.

(B) The hydrogenation of step (b)i) or (b) is carried out in the presence of an inert diluent and a hydrogenation catalyst.

Particularly preferred is a process in which the hydrogenation is carried out in a temperature range from 0° C. to 100° C., preferably from 15° C. to 75° C., particularly from 30° C. to 60° C.

Also preferred is a process wherein the hydrogenation is carried out under a pressure of more than 0.5 bar to 100 bar, preferably under a pressure of 1 bar to 10 bar, particularly at about 1-4 bar.

The inert diluents may be both protic solvents—such as e.g. alcohols, carboxylic acids and/or water, or aprotic polar solvents such as e.g. ethers and/or amides or lactams and/or mixtures thereof. Water may optionally be added to all the solvents. The protic solvents used are preferably branched or unbranched $C_1$-$C_8$ alkanols, $C_1$-$C_3$ carboxylic acids or mixtures thereof. Particularly preferably, lower alcohols such as methanol, ethanol, n-propanol and isopropanol, carboxylic acids such as formic acid, acetic acid and propionic acid or mixtures thereof are used. It is particularly preferably to use as the reaction medium ethanol and/or acetic acid, which may optionally contain water. Suitable aprotic solvents include polar ethers such as for example tetrahydrofuran, dioxane or dimethoxyethylether or amides such as for example dimethylformamide, or lactams such as for example N-methylpyrrolidone. Preferably, solvents with a low tendency to flammability are used.

Suitable hydrogenation catalysts are generally transition metals such as for example nickel, platinum or palladium or the salts or oxides thereof. Raney nickel, platinum oxide and palladium on an inert carrier material, particularly palladium on activated charcoal (Pd/C) are preferred.

Processes in which the product of step (a) is used in a ratio by weight to the hydrogenation catalyst of 1:1 to 1000:1, preferably from 5:1 to 100:1 during hydrogenation are preferred.

In a preferred embodiment of step (b) the product of step (a) is taken up in ethanol and after the addition of acetic acid and at 2 bar hydrogen it is hydrogenated with water-moistened 10% Pd/C at ambient temperature. The catalyst is filtered off and p-toluenesulphonic acid, dissolved in 90 ml of ethanol or in 90 ml of water, is added. Preferably an aqueous p-toluenesulphonic acid solution is used. The tosylate of the 4-(benzimidazol-2-ylmethylamino)-benzamidine obtained is precipitated, filtered off and washed with ethanol in several batches.

In a particularly preferred embodiment of step (b) the product of step (a) is taken up in ethanol/water and at 4 bar hydrogen hydrogenated with water-moistened 10% Pd/C at 60° C. The catalyst is filtered off and p-toluenesulphonic acid (solid or dissolved in 90 ml of ethanol or in 90 ml of water) is added. Preferably, solid p-toluenesulphonic acid is used. The tosylate of the 4-(benzimidazol-2-ylmethylamino)-benzamidine obtained is precipitated, filtered off and washed with ethanol in several batches.

In a preferred embodiment of step (b)i) the product of step (a) is taken up in a mixture of THF and water (approx. 7:3 based on the volume) and hydrogenated at 4 bar hydrogen with water-moistened 10% Pd/C at approx. 40° C. The hydrogenating solution is filtered and the filter is washed with THF/water (7:3). The filtrate is diluted with THF and water and combined with potassium carbonate.

Then, according to one variant of the process, the carbonylation in step (b)ii) may be carried out directly. To do this, after separation of the catalyst without intermediate isolation of the hydrogenation product, the filtrate is combined with an auxiliary base and reacted with a carbonylation agent. The carbonylation agents and bases which may be used as well as possible solvents and suitable temperature ranges are described in more detail under (E). The reaction is preferably carried out with potassium carbonate and at temperatures between 10-50° C., preferably 10-20° C.

After the reaction has ended the suspension is heated to approx. 50° C., for example, so that a clear two-phase mixture is formed. The lower, aqueous phase has a high inorganic load and can be separated off before the THF is distilled off and the solvent is exchanged for acetone, from which the compound of formula (I) is crystallised by the addition of water.

Possible variant of the working up:

In a variant of the reaction, after the separation of the inorganically loaded aqueous phase and distillation of THF, the solvent may be exchanged for butyl acetate. The crystallisation of the compound of formula (I) is then carried out after aqueous extraction of the organic phase and azeotropic elimination of the residual moisture.

(C) In order to prepare 2-[4-(1,2,4-oxadiazol-5-on-3-yl)-phenylamino]-acetic acid, 2-[4-(1,2,4-oxadiazol-5-on-3-yl)-aniline is reacted with a 2-haloacetic acid ester, preferably ethyl bromoacetate, in the presence of a weak base, preferably a tertiary amine, such as for example triethylamine or an alkali metal carbonate, such as for example sodium carbonate in an inert solvent, and the 2-[4-(1,2,4-oxadiazol-5-on-3-yl)-phenylamino]-acetic acid ester obtained is saponified.

The inert diluents used may be both protic solvents—such as e.g. alcohols, and/or water—or aprotic polar solvents such as e.g. ethers and/or amides or lactams and/or mixtures thereof. Water may optionally be added to all the solvents. Protic solvents used are preferably water or branched or unbranched $C_1$-$C_8$ alkanols or mixtures thereof. Particularly preferably, water or lower alcohols such as methanol, ethanol, n-propanol and isopropanol or mixtures thereof are used. Most particularly preferably, ethanol is used as reaction medium, and this may optionally contain water. Isopropanol, optionally together with water, may also be used. The most suitable solvent is water, however. Suitable aprotic solvents are polar ethers such as for example tetrahydrofuran or dimethoxy-ethylether or amides such as for example dimethylformamide, or lactams such as for example N-methylpyrrolidone.

In a particularly preferred embodiment ethyl bromoacetate is metered into a suspension of 2-[4-(1,2,4-oxadiazol-5-on-3-yl)-aniline and sodium carbonate in water/isopropanol or preferably in water/ethanol and stirred at 35-45° C. The cooled suspension is suction filtered, washed with water and ethanol in several batches and dried.

The saponification is preferably carried out in a protic solvent with an alkali metal or alkaline earth metal hydroxide, particularly with lithium, sodium or potassium hydroxide.

In a particularly preferred embodiment 2-[4-(1,2,4-oxadiazol-5-on-3-yl)-phenylamino]-acetic acid ester is suspended in water or preferably in water/ethanol and slowly combined with an aqueous solution of NaOH at ambient temperature. The suspension changes into a solution and is heated to 45 to 75° C. HCl is added to the solution thus obtained until a pH of about 5 or preferably pH 3 is achieved. The solid is isolated and washed with cold water and cold ethanol and MtBE.

(D) In order to prepare 2-[4-(1,2,4-oxadiazol-5-on-3-yl)-aniline, 4-aminophenyl-amidoxime is reacted with a dialkyl carbonate, preferably dimethyl carbonate or diethyl carbonate in the presence of a base, preferably an alkali metal alkoxide, particularly sodium methoxide, sodium ethoxide or potassium tert-butoxide.

4-aminophenyl-amidoxime may be prepared e.g. by reacting 4-aminobenzonitrile with hydroxylamine hydrochloride.

In a particularly preferred embodiment sodium methoxide or preferably sodium ethoxide is added at 65-75° C., preferably at 70-75° C., to a suspension of 4-aminophenyl-amidoxime in ethanol and rinsed with ethanol. After 15 min stirring diethyl carbonate or preferably dimethyl carbonate is added dropwise. After 2-4 hours reaction time the mixture is cooled and ethanol is distilled off at 120 mbar and 40° C. The residue is taken up in water and after heating adjusted to pH 10-12 using semi-conc. sodium hydroxide solution, then to pH <6, preferably to pH<4, particularly preferably to pH 2-3, by acidifying with conc. hydrochloric acid, and slowly cooled. The solution changes into a suspension, which is filtered and washed several times with cold water and ethanol.

(E) In order to prepare a salt of a compound of formula (I), wherein $R^3$ has a meaning other than hydrogen, by carbonylation of a compound of formula (I), wherein $R^3$ denotes hydrogen, and precipitation of the desired salt without prior isolation of the carbonylation product, in a first partial step (c)i) the compound of formula (I), wherein $R^3$ denotes hydrogen, is reacted with a carbonylation agent $R^3$—X, where $R^3$ has the meanings given above, with the exception of hydrogen, and X denotes a leaving group. Preferably X may represent a halogen such as for example chlorine or bromine or a p-toluenesulphonyl, methanesulphonyl or trifluoromethanesulphonyl group. Most particularly preferred is n-hexylchloroformate for preparing a compound of formula (I) wherein $R^3$ denotes n-hexyl. The reaction is preferably carried out at a temperature of 10 to 50° C., in particular at 10 to 20° C. in the presence of a base. The base used may conveniently be an alkali metal carbonate such as for example potassium carbonate or sodium carbonate, an alkali metal hydrogen carbonate such as for example sodium hydrogen carbonate or potassium hydrogen carbonate or a tertiary amine such as for example triethylamine. Preferably potassium carbonate is used. The reaction may for example be carried out in mixtures of water and acetone or water and THF; a water/acetone mixture is preferred.

After the reaction has ended a clear two-phase mixture may be formed by heating the suspension, e.g. to approx. 50° C., so that the aqueous phase, which contains a large proportion of the inorganic constituents, can easily be separated off.

Then a change of solvent may take place. Suitable solvents include for example ketones or esters such as MIBK, butyl acetate, ethyl acetate, propyl acetate, isopropyl acetate or isobutyl acetate. Particularly preferred are MIBK and butyl acetate. The organic phase is washed under aqueous conditions, to eliminate polar impurities. Any residual moisture remaining is subsequently removed by azeotropic distillation before the product is crystallised and isolated or e.g. combined with acetone for the partial step c)ii), however, without intermediate isolation and then, by the addition of the corresponding acid, for example methanesulphonic acid, for preparing the methanesulphonate, the desired salt is precipitated and isolated directly.

(F) In order to precipitate a specific salt starting from the compound of formula (I) a solution of the compound of formula (I) is optionally prepared with heating and then the corresponding acid is added, optionally as a solution. In order to crystallise the salt the mixture may be cooled. Then the salt is isolated. Suitable solvents include for example acetone or a mixture of acetone and ethanol.

Optionally the amount of solvent used for preparing the substrate solution may be increased. This allows clear filtration of the solution before the addition of the acid.

The preparation of the 2-[4-(1,2,4-oxadiazol-5-on-3-yl)-phenylamino]-acetic acid needed as intermediate product from 4-aminobenzonitrile is illustrated in the following reaction plan:

(The non-isolated intermediate stages indicated by square brackets may optionally vary between the different process variants. A preferred embodiment is shown.)

Diagram I

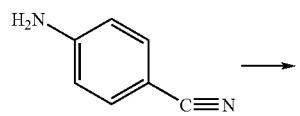

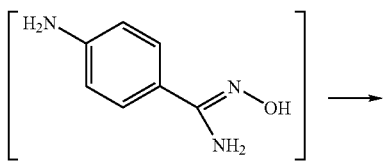

(1A)

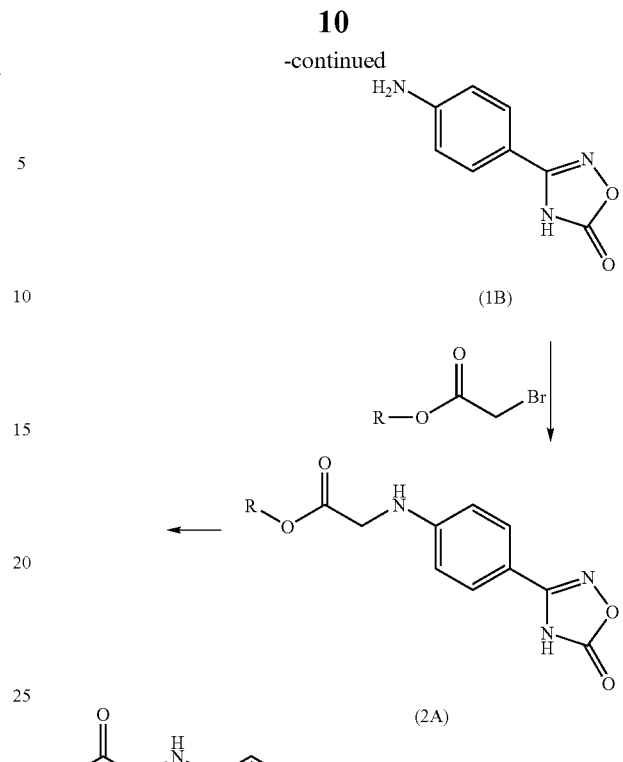

The preparation of a 4-(benzimidazol-2-ylmethylamino)-benzamidine is shown by way of example in the following reaction plan:

Diagram II

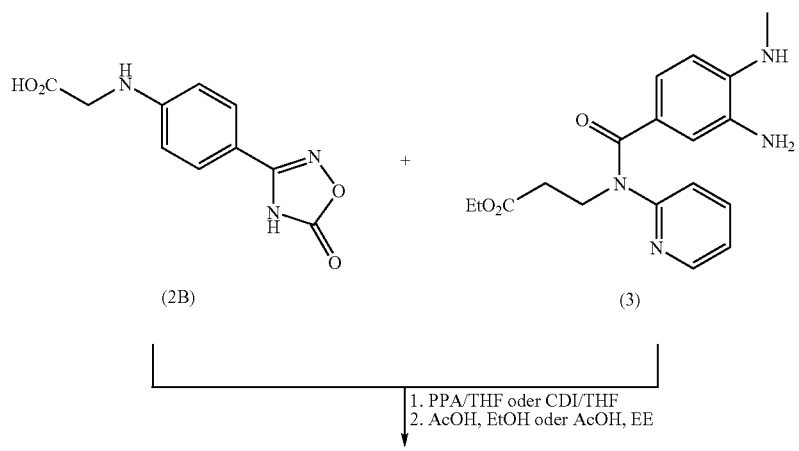

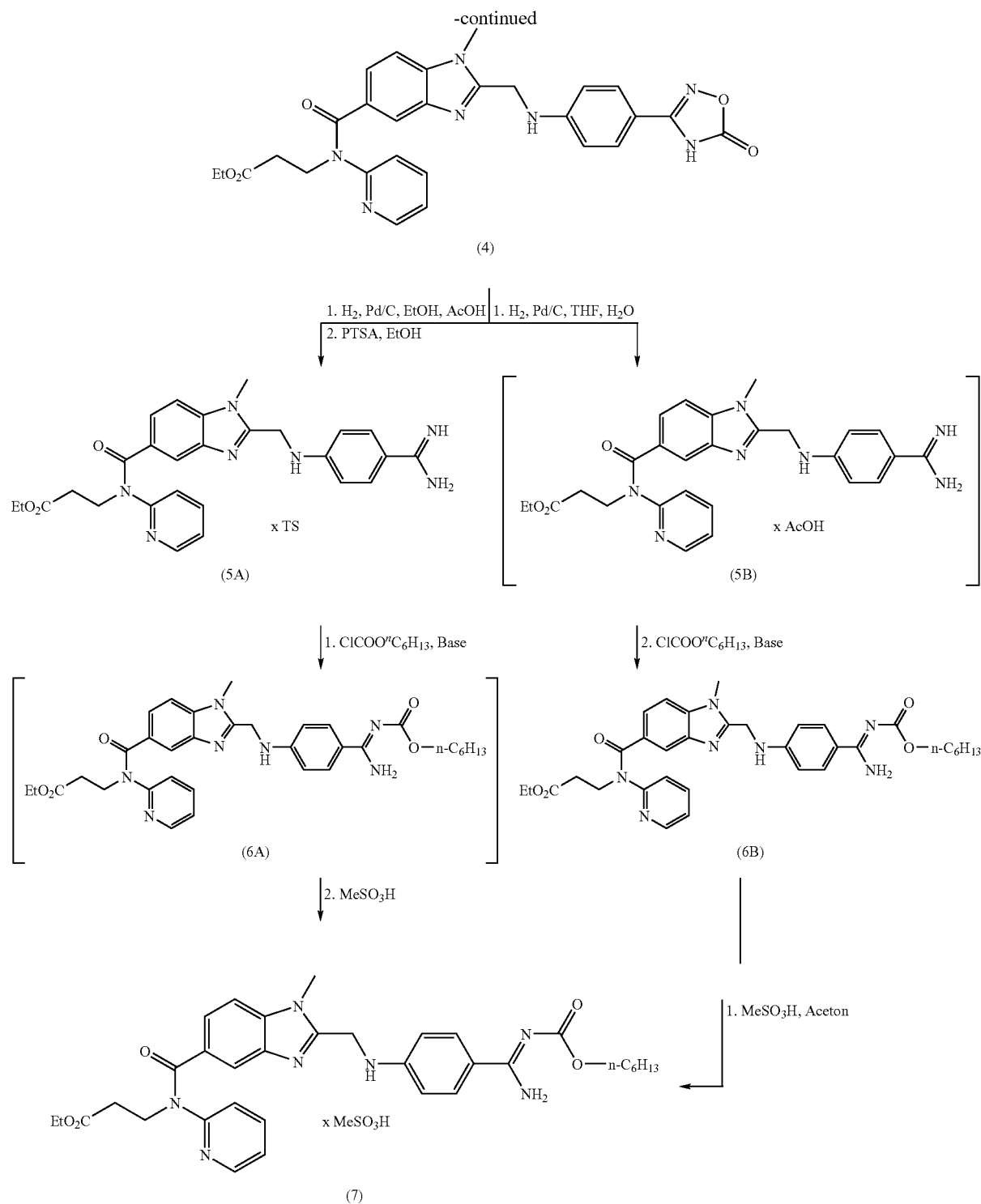

The working up of the individual reactions may take place in the conventional manner, for example, by separating off the reaction adjuvants, eliminating the solvent and isolating pure end product from the residue by crystallisation, distillation, extraction or chromatography.

Following the process described above the compound of formula (I) thus obtained may be converted into a physiologically acceptable salt. The physiologically acceptable salts may be salts with inorganic or organic acids or, if the compound contains a carboxy group, with inorganic or organic bases. Examples of acids for this purpose include methanesulphonic acid, hydrochloric acid, hydrobromic acid, sulphuric acid, phosphoric acid, fumaric acid, succinic acid, lactic acid, citric acid, tartaric acid or maleic acid. Examples of bases which may be used include sodium hydroxide, potassium hydroxide, cyclohexylamine, ethanolamine, diethanolamine and triethanolamine. The compound of formula (6) is preferably converted into its mesylate.

The process according to the invention will now be illustrated by means of the following Examples. The skilled man is aware that the Examples serve only as an illustration and are not to be regarded as restrictive.

EXAMPLES

The following abbreviations are used hereinbefore and hereinafter:
AcOH acetic acid
AMBPA 3-amino-4-methylaminobenzoic acid-N-(2-pyridyl)-N-(2-ethoxycarbonylethyl)-amide
CDI 1,1'-carbonyldiimidazole
DIPEA diisopropylethylamine
EE ethyl acetate
EtOH ethanol
HCl hydrochloric acid
MIBK methylisobutylketone (4-methyl-2-pentanone)
MtBE methyl-tert-butylether
NaOH sodium hydroxide
NMP N-methylpyrrolidone
PPA propanephosphonic anhydride
PTSA p-toluenesulphonic acid
RT room temperature
THF tetrahydrofuran
decomp. decomposition

Example 1

Preparation of 2-[4-(1,2,4-oxadiazol-5-on-3-yl)-aniline (1)

Variant 1:
(1A)

In the reaction vessel are placed 118.6 g (1 mol) 4-aminobenzonitrile and 68.9 g (0.65 mol) sodium carbonate in 500 ml of ethanol and 100 ml of water and the mixture is heated to 60° C. 76.4 g (1.1 mol) hydroxylamine-hydrochloride, dissolved in 100 ml of water, are slowly added dropwise to this suspension.

The mixture is subsequently stirred overnight at 60° C. During cooling to 0-5° C. the substance is precipitated, filtered off and washed several times with a total of 150 ml cold water and 100 ml cold ethanol. Finally the mixture is washed with 50 ml MtBE and 178.4 g moist product are obtained. This is dried at 35° C. in vacuo.

Yield: 135.4 g light beige substance (89.5% of theory), melting point: from 169.5° C. (decomp.); purity: >98% HPLC peak area
(1B)

25.02 g (0.46 mol) sodium methoxide are added batchwise to a suspension of 60.5 g (1A) (0.4 mol) in 400 ml of ethanol at 70-75° C. and rinsed with 20 ml of ethanol.

After 15 min stirring 47.25 g (0.4 mol) diethyl carbonate are added dropwise. After 3 hours' reaction the mixture is cooled to 40° C. and the ethanol is distilled off at 120 mbar and 40° C. A dark residue is obtained. This is dissolved at 40-45° C. in 350 ml of water and after heating to 70° C., first adjusted to pH 11 by the slow addition of semi-conc. sodium hydroxide solution; then to pH 5.5 by acidifying with conc. hydrochloric acid, and slowly cooled. The solution goes into a suspension, which is filtered and washed several times with a total of 150 ml cold water and 50 ml of ethanol.

88.7 g moist substance are obtained, which is dried at 35° C. in vacuo.

Yield: 62 g dark substance (87.5% of theory); melting point: from 178° C. (decomp.); purity: >98% HPLC peak area Variant 2:
(1A)

In the reaction vessel are placed 41.3 g (0.35 mol) 4-aminobenzonitrile and 36.5 g (0.53 mol) hydroxylamine-hydrochloride in 175 ml of ethanol and the mixture is heated to 60° C. 170.1 g (0.53 mol) sodium ethoxide solution (~21% in ethanol) are slowly added dropwise to this suspension.

The mixture is subsequently stirred overnight at 60° C. During cooling to 0-5° C. the substance is precipitated, filtered off and washed several times with a total of 70 ml cold ethanol. Approx. 86 g moist product are obtained. This is further processed directly.
(1B)

32 g (0.35 mol) dimethyl carbonate are added to a suspension of 86 g (1A) in 270 ml of ethanol. At 65-75° C., 125 g (0.38 mol) sodium ethoxide solution (~21% in ethanol) are added and rinsed with 20 ml of ethanol.

After 3 hours' reaction the mixture is cooled to 40° C. and the ethanol is distilled off at 120 mbar and 40° C. A dark residue is obtained. This is dissolved at 40-45° C. in 280 ml of water and after heating to 70° C. adjusted first to pH 11 by the slow addition of semi-conc. sodium hydroxide solution; then to pH 3-4 or preferably to pH 2-3 by acidifying with conc. hydrochloric acid and slowly cooled. The solution goes into a suspension, which is filtered and washed several times with a total of 50 ml cold water and 20 ml of ethanol.

Approx. 88 g moist substance are obtained, which is dried at max. 50° C. in vacuo.

Yield: 48 g beige substance (77.5% of theory); melting point: from 178° C. (decomp.); purity: >98% HPLC peak area

Example 2

Preparation of 2-[4-(1,2,4-oxadiazol-5-on-3-yl)-phenylamino]-acetic acid (2)

Variant 1:
(2A)

At ambient temperature 83.5 g (0.5 mol) ethyl bromoacetate are metered into a suspension of 70.86 g (0.4 mol) (1B) and 26.5 g (0.25 mol) sodium carbonate in 600 ml of water/isopropanol and stirred overnight. The reaction mixture is reddish-brown to orange. The suspension cooled to 0° C. is suction filtered, washed in several batches with 300 ml of water and 150 ml of ethanol (106 g moist light-brown substance) and dried at 35° C. in vacuo.

Yield: 92.44 g brownish substance (87.7% of theory) melting point: from 186.1° C. (decomp.); purity: >98% HPLC peak area
(2B)

The ester (2A) (86.9 g; 0.33 mol) thus obtained is suspended in 400 ml of water and at RT 120 g of 45% NaOH are slowly added dropwise. The suspension goes into solution and is reddish (pH 12.5). It is heated to ~60° C. and saponified for 1 h. The solution obtained is combined batchwise with HCl (37% or preferably with conc. HCl), until pH 5 is obtained. It is cooled to 0° C. The solid is suction filtered and washed in several batches with a total of 400 ml cold water as well as 40 ml cold ethanol and MtBE. 81.4 g moist dark substance are obtained. It is dried at 35° C. in vacuo.

Yield: 76.7 g substance (98% of theory)
melting point: from 193° C. (decomp.)
purity: >99% HPLC peak area
Variant 2:
(2A)

At 45° C. 60.2 g (0.36 mol) ethyl bromoacetate are metered into a suspension of 53.2 g (0.3 mol) (1B) and 19.1 g (0.18 mol) sodium carbonate in 500 ml of water/ethanol (90:10 to 95:5) and optionally stirred overnight. The reaction mixture is reddish-brown to orange. The suspension cooled to 0° C. is suction filtered, washed in several batches with 100 ml of ethanol and dried at max. 50° C. in vacuo.

Yield: 69.5 g brownish-beige substance (87.7% of theory); melting point: from 186.1° C. (decomp.); purity: >98% HPLC peak area (2B)

The ester (2A) (86.9 g; 0.33 mol) thus obtained is suspended in 400 ml of water or preferably ethanol/water (1:1) and at RT 120 g of 45% NaOH are slowly added dropwise. The suspension goes into solution and is reddish (pH 12.5). It is heated to ~60° C. and saponified for 1 h. The solution obtained is combined batchwise with HCl (37% or preferably with conc. HCl), until a pH 3 is obtained. It is cooled to 0° C. The solid is suction filtered and washed in several batches with a total of 400 ml cold water as well as 40 ml cold ethanol. 81.4 g moist substance are obtained. It is dried at 35° C. in vacuo.

Yield: 76.7 g substance (98% of theory)
melting point: from 193° C. (decomp.)
purity: >99% HPLC peak area Example 3

Preparation of 3-amino-4-methylaminobenzoic acid-N-(2-pyridyl)-N-(2-ethoxycarbonylethyl)-amide (AMBPA) (3)

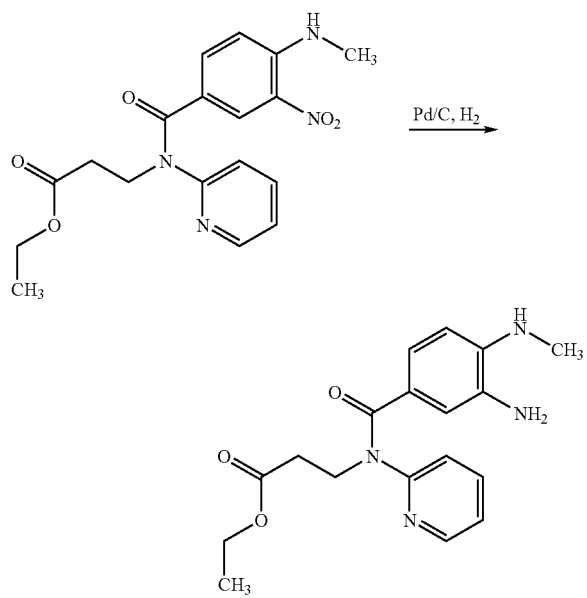

Variant A: Pd/C 5%

150 g (0.4 mol) 4-methylamino-3-nitrobenzoic acid-N-(2-pyridyl)-N-(2-ethoxycarbonylethyl)-amide, 12 g 5% palladium on charcoal catalyst and 627 ml of ethyl acetate are placed in a hydrogenating autoclave. The mixture is hydrogenated under a hydrogen atmosphere of 3-4 bar at 35-55° C. until the hydrogen uptake is constant (1-2 h). After cooling to 20° C. the hydrogenating solution is filtered off from the catalyst and evaporated down in vacuo using the rotary evaporator. The residue is taken up in 650 ml isopropanol, distilled down to half the original volume and cooled to 5-10° C. After 4 h the resulting suspension is filtered, and the precipitate thus isolated is washed batchwise with a total of 100 ml isopropanol. The solid obtained is dried in the vacuum dryer at 50° C.

Yield: 114.2 g (corr. 83% of theory)
Variant B: Pd/C 10%

25 g (0.07 mol) 4-methylamino-3-nitrobenzoic acid-N-(2-pyridyl)-N-(2-ethoxycarbonylethyl)-amide, 2.5 g 10% palladium on charcoal catalyst and 83 ml of ethyl acetate are placed in a hydrogenating autoclave. The mixture is hydrogenated under a hydrogen atmosphere of 3-4 bar at 50° C. until the hydrogen uptake is constant (4-5 h). After cooling to 20° C. the hydrogenating solution is filtered off from the catalyst and evaporated down in vacuo using the rotary evaporator. The residue is dissolved warm in a little ethyl acetate and combined with 68 ml of toluene. After cooling to 5° C. the mixture is left for 1 h with stirring, then the precipitate is filtered off and washed with toluene. The product obtained is dried at 40° C. in the vacuum dryer.

Yield: 20.9 g (con. 91% of theory)

Example 4

Preparation of 1-methyl-2-[N-[4-(1,2,4-oxadiazol-5-on-3-yl)phenyl]-amino-methyl]-benzimidazol-5-yl-carboxylic acid-N-(2-pyridyl)-N-(2-ethoxycarbonyl-ethyl)-amide (4)

Variant A: CDI as Coupling Reagent 11.35 g (70 mmol) 1,1'-carbonyldiimidazole are suspended in 100 ml THF and heated to 50° C. 14.23 g (60.5 mmol) (2B) are added batchwise. 17.1 g (50 mmol) AMPBA are dissolved in 37 ml THF with heating to 50° C.

After approx. 90 min the suspension is metered into the solution of AMPBA and rinsed with 20 ml THF.

The reaction mixture is stirred for approx. 18 h and subsequently, after the addition of 100 ml acetic acid, refluxed, so that the THF is distilled off. After approx. 1 h the mixture is combined with 400 ml of water and stirred.

The solution is cooled, the pink solid substance precipitated is filtered off and washed with 20 ml of water in 2 batches and dried at a maximum of 50° C. in vacuo.

Yield: 24.8 g substance (75% of theory); melting point: from 167° C. with decomp. (DSC); purity: >95% HPLC peak area
Variant B: PPA as Coupling Reagent 34.2 g (0.1 mol) AMBPA, 27.5 g (0.12 mol) (2B) and 30.3 g (0.23 mol) DIPEA are placed in 170 ml THF and cooled to somewhat below ambient temperature.

Now 85 g (0.13 mol) PPA (as ~50% solution in ethyl acetate) are metered in. The mixture is stirred for another 90 min and then the solvent is distilled off. Towards the end 73.5 g acetic acid are added and the mixture is heated to an internal temperature of 90° C. Then 400 ml of ethanol or preferably 400 ml of ethanol/water (approx. 85:15) and kieselguhr filtering adjuvant (e.g. Clarcel®) are added and the mixture is filtered hot. The solution is cooled, the solid substance precipitated is filtered off and washed in 2 batches with 50 ml of ethanol and dried at max. 50° C. in vacuo.

Yield: 56 g substance (85% of theory); melting point: from 167° C. with decomp. (DSC); purity: >95% HPLC peak area
Variant C: Pivaloyl Chloride as Coupling Reagent 96 g (0.41 mol) (2B) are suspended in 250 ml NMP and 550 ml THF at 0° C. The thin suspension is combined successively with 48 g (0.4 mol) pivaloyl chloride and 52 g (0.4 mol) DIPEA and stirred for 30 minutes. Then 125 g (0.36 mol) AMBPA dissolved in 800 ml acetic acid are added and the reaction mixture is refluxed for 3 h. THF is distilled off under a gentle vacuum and 1600 ml of water are metered in with heating. The solid is isolated at 5° C., washed with 550 ml of water and dried overnight in the circulating air dryer at max. 50° C.

Yield: 183 g (76%)
purity: >95% HPLC peak area

Example 5

Preparation of 1-methyl-2-[N-[4-amidinophenyl]-amino-methyl]-benzimidazol-5-yl-carboxylic acid-N-(2-pyridyl)-N-(2-ethoxycarbonylethyl)-amide (5A)

Variant A: Hydrogenation of (4) in Ethanol 37.3 g (56.4 mmol) (4) are dissolved in 900 ml of ethanol and after the addition of 10 ml acetic acid the mixture is hydrogenated at 2 bar hydrogen with 4 g water-moistened 10% Pd/C at RT. The catalyst is filtered off and 17 g (89.4 mmol) PTSA, dissolved in 180 ml of ethanol are added. The tosylate of (5A) is precipitated, filtered off and washed in several batches with 150 ml of ethanol.

Moist substance is obtained, which is dried in vacuo at 35° C.

Yield: 34.5 g light beige substance (91.3% of theory); melting point: 187° C. (DSC); purity: >98% HPLC peak area.
Variant B: Hydrogenation of (4) in Ethanol/Water 37.3 g (56.4 mmol) (4) are dissolved in 400 ml of ethanol/water (90:10) and hydrogenated at 4 bar hydrogen with 4 g water-moistened 10% Pd/C at 60° C. The catalyst is filtered off and 11.5 g (60.6 mmol) PTSA are added. During evaporation the tosylate of (5A) is precipitated. The suspension is cooled, the substance is filtered off and washed in several batches with 150 ml of ethanol/water.

Moist substance is obtained, which is dried in vacuo at 35° C.

Yield: 33.7 g light beige substance (89% of theory); melting point: 187° C. (DSC); purity: >98% HPLC peak area.
Variant C: Hydrogenation of (4) in THF/Water 30.0 g (45.3 mmol) (4) are dissolved in 90 ml THF/water (1:1) at ambient temperature, combined with 4 g water-moistened 10% Pd/C and hydrogenated at 4 bar and 60° C. The catalyst is filtered off, washed with approx. 40 ml THF/water (1:1) and the filtrate is fed into the next step without working up or is isolated as described above by the addition of 13.6 g (72 mmol) PTSA, dissolved in 100 ml of water, and cooling.

Example 6

Preparation of 1-methyl-2-[N-[4-(N-n-hexyloxycarbonylamidino)phenyl]-amino-methyl]-benzimidazol-5-yl-carboxylic acid-N-(2-pyridyl)-N-(2-ethoxycarbonylethyl)-amide (6B)

The compound obtained according to Example 4 is reacted with n-hexylchloroformate in the presence of a base in known manner.
Variant A: Acylation of (5A) in Acetone/Water 55 g (81.9 mmol) (5A), dissolved in 437 ml acetone and 273 ml of water, are combined with 16.4 g (99.6 mmol) n-hexylchloroformate in the presence of 34 g (246 mmol) potassium carbonate at a temperature of approx. 15° C. After the end of the reaction the precipitated product is filtered off and washed with acetone/water. If necessary it may be dissolved again in approx. 270 ml acetone with heating and subsequently filtered. After filtration the substance is crystallised again by addition of 220 ml of water.

The isolated substance is dried at 45° C. in vacuo.
Yield: 42-48 g (82-94%)
Variant B: Acylation of (5A) in Acetone/Water with Phase Separation 50 g (74.4 mmol) 5A, suspended in 380 ml acetone and 248 ml of water, are combined with 13.48 g (81.9 mmol) n-hexylchloroformate in the presence of 63 g (447 mmol) potassium carbonate at a temperature of approx. 15° C. After the end of the reaction the suspension is heated to about 50° C. After the phase separation the aqueous phase is discarded and the acetone is replaced by 450 ml butyl acetate. The aqueous phase then separated off is discarded and the organic phase is washed with water in several batches. After the organic phase has been dried by azeotropic distillation the product is crystallised at approx. 60-80° C., isolated and washed with butyl acetate. The product is dried at 60° C. in vacuo.

Yield: 47 g (87%)
purity: >99% HPLC peak area
Variant C: Acylation of (5A) in Acetone/Water with Phase Separation in on the kg Scale 40 Kg (59.5 mol) 5A are suspended together with 50.4 kg (365 mol) potassium carbonate in 300 l acetone and 200 l water. 10.8 kg (65.6 mol) n-hexylchloroformate are metered into the suspension within 1 h at approx. 15° C. and after 30 min stirring the suspension is heated to 50° C. After separation of the aqueous phase acetone is replaced by butyl acetate. The aqueous phase that separates off is discarded and the organic phase is extracted twice with water. After the organic phase has been dried by azeotropic distillation the product 6B is crystallised, isolated and washed with butyl acetate. The product is dried at 60° C. in vacuo.

Yield: 30.5 kg (82%)
purity: >99% HPLC peak area

Example 7

Preparation of 1-methyl-2-[N-[4-(N-n-hexyloxycarbonylamidino)phenyl]-amino-methyl]-benzimidazol-5-yl-carboxylic acid-N-(2-pyridyl)-N-(2-ethoxycarbonylethyl)-amide (6B) from 1-methyl-2-[N-[4-(1,2,4-oxadiazol-5-on-3-yl)phenyl]-amino-methyl]-benzimidazol-5-yl-carboxylic acid-N-(2-pyridyl)-N-(2-ethoxycarbonylethyl)-amide (4)

60 g (91 mmol) 1-methyl-2-[N-[4-(1,2,4-oxadiazol-5-on-3-yl)phenyl]-amino-methyl]-benzimidazol-5-yl-carboxylic acid-N-(2-pyridyl)-N-(2-ethoxycarbonylethyl)-amide (4) are hydrogenated with 3.0 g 10% palladium on charcoal (moistened with water) in 126 ml THF and 54 ml of water at 40° C. under 4 bar excess hydrogen pressure for 25 min. The hydrogenation solution is filtered and the filter is washed with 75 g THF/water (7:3). The filtrate is combined successively with 56 ml THF, 260 ml of water and batchwise with 75.2 g (544 mmol) potassium carbonate at ambient temperature. Then 14.2 g (86 mmol) of n-hexylchloroformate are metered in over 40 min. After the conversion level has been checked a further 1.2 g (7.3 mmol) n-hexylchloroformate are metered in, so that all the starting material is reacted. The suspension is heated to approx. 45° C. A clear two-phase mixture is formed. The aqueous phase is discarded and the THF is largely distilled off. 150 ml acetone are added to the suspension, it is heated to 50° C. and filtered clear. The filter is rinsed with 100 ml acetone. The filtrate is cooled to ambient temperature and the product is precipitated by the slow addition of 100 ml of water. The moist product is washed with 150 ml acetone/water (1:1) and 150 ml of water and dried in vacuo.
Yield: 56.9 g (94%)
HPLC-purity: >98.8%

Example 8

Preparation of 1-methyl-2-[N-[4-(N-n-hexyloxycarbonylamidino)phenyl]-amino-methyl]-benzimidazol-5-yl-carboxylic acid-N-(2-pyridyl)-N-(2-ethoxycarbonylethyl)-amide mesylate (7)

100 g (0.16 mol) of the compound (6B) are dissolved in 890 ml acetone with heating and combined with a solution of 15 g (0.16 mol) methanesulphonic acid in 200 ml acetone. The solution is filtered and after the addition of 77 ml acetone cooled to approx. 20° C. The precipitated product is isolated and washed with acetone.
Then the mixture is dried at max. 50° C. in the vacuum dryer.
Yield: 90-98% (103-113 g)

Example 9

Preparation of 1-methyl-2-[N-[4-(N-n-hexyloxycarbonylamidino)phenyl]-amino-methyl]-benzimidazol-5-yl-carboxylic acid-N-(2-pyridyl)-N-(2-ethoxycarbonylethyl)-amide mesylate (7) from 1-methyl-2-[N-[4-amidinophenyl]-amino-methyl]-benzimidazol-5-yl-carboxylic acid-N-(2-pyridyl)-N-(2-ethoxycarbonylethyl)-amide (5A)

In the reaction vessel 50.0 g (74.4 mmol) 5A and 63.0 g (446.6 mmol) potassium carbonate are suspended in 380 ml acetone and 248 ml of water and at 20° C. 13.48 g (81.9 mmol) of n-hexylchloroformate are metered in within 1 h. After 30 min further reaction the suspension is heated to approx. 50° C. A clear two-phase mixture is formed, into which another 0.12 g (0.7 mmol) n-hexylchloroformate are metered after the conversion level has been checked, so that all the starting material is reacted. The aqueous phase is separated off, the organic phase is filtered clear and the filter is washed with 50 ml acetone. Under a slight vacuum 300 ml acetone are distilled off and replaced by 250 ml MIBK. The aqueous phase that settles out is separated off and the organic phase is extracted at 50-60° C. with 50 ml of water. Then 300 ml solvent are distilled off and replaced by 500 ml acetone. The reaction solution is cooled to 30-36° C., 7 seed crystals are added (obtained for example from an earlier reaction according to Example 7 or according to the method described in Example 3 of WO 03/074056) and a previously prepared solution of 6.44 g (67 mmol) methanesulphonic acid in 50 ml acetone is added dropwise. The suspension is stirred for 20 min, the product is isolated by filtration and washed with 300 ml acetone. The isolated substance is dried at 45° C. in vacuo.
Yield: 48.0 g (89%)
purity: >99% HPLC peak area

What is claimed is:
1. A process for preparing an optionally substituted 4-benzimidazol-2-ylmethylamino)-benzamidine of formula (I)

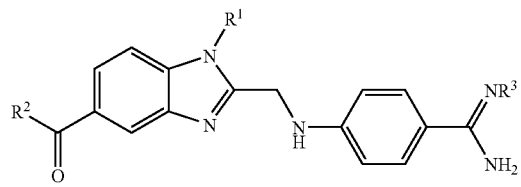

wherein
$R^1$ denotes a methyl group,
$R^2$ denotes an $R^{21}NR^{22}$ group, wherein
$R^{21}$ denotes an ethyl group which is substituted by an ethoxycarbonyl group, and
$R^{22}$ denotes a pyridin-2-yl group,
$R^3$ denotes an n-hexyloxycarbonyl group;
comprising the steps of:
(a) reacting a phenyldiamine of formula (II)

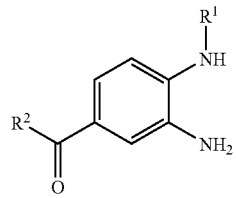

wherein $R^1$ and $R^2$ have the meanings given for formula (I), with 2-[4-(1,2,4-oxadiazol-5-on-3-yl)-phenylamino]-acetic acid to form a product of formula (III)

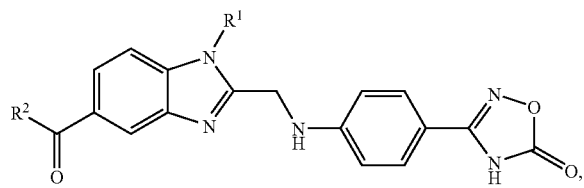

wherein $R^1$ and $R^2$ have the meanings given for formula (I),
(b) (i) hydrogenating the product of formula (III); and
(ii) reacting the product of step (b)(i), without any prior isolation, with a compound of formula (IV), $R^3$—X (IV)

wherein $R^3$ has the meaning given hereinbefore and X denotes a suitable leaving group.
2. Process according to claim 1, characterised in that the compound of formula (I) thus obtained is subsequently converted into a physiologically acceptable salt.
3. Process according to claim 2, characterised in that the physiologically acceptable salt is the methanesulphonate.

* * * * *